US00PP30234P3

(12) United States Plant Patent
Miller

(10) Patent No.: US PP30,234 P3
(45) Date of Patent: Feb. 26, 2019

(54) ***LEUCADENDRON* PLANT NAMED 'WILD THING'**

(50) Latin Name: *Leucadendron salignum x laureolum*
Varietal Denomination: WILD THING

(71) Applicant: Luen Miller, Soquel, CA (US)

(72) Inventor: Luen Miller, Soquel, CA (US)

( * ) Notice: Subject to any disclaimer, the term of this patent is extended or adjusted under 35 U.S.C. 154(b) by 0 days.

(21) Appl. No.: 15/731,608

(22) Filed: Jul. 8, 2017

(65) Prior Publication Data

US 2019/0014701 P1 Jan. 10, 2019

(51) Int. Cl.
*A01H 5/00* (2018.01)

(52) U.S. Cl.
USPC ..... Plt./226

(58) Field of Classification Search
USPC ..... Plt./263.1, 226
See application file for complete search history.

*Primary Examiner* — Susan McCormick Ewoldt
(74) *Attorney, Agent, or Firm* — Cassandra Bright

(57) ABSTRACT

A new and distinct *Leucadendron salignum* x *laureolum* cultivar named 'WILD THING' is disclosed, characterized by yellow-green foliage. The new cultivar is a *Leucadendron, salignum* x *laureolum* typically suited for ornamental container and garden use.

1 Drawing Sheet

Latin name of the genus and species: *Leucadendron salignum* x *laureolum.*

Variety denomination: 'WILD THING'.

BACKGROUND OF THE INVENTION

The new variety originated as a chance discover by the inventor, Luen Miller. The variety was discovered as a naturally occurring branch mutation on a single plant of *Leucadendron salignum* x *laureolum* 'Ebony' U.S. Plant Pat. No. 23,258. The new variety was discovered during June of 2011 at a homeowner garden in Los Gatos, Calif.

After selecting and isolating the new cultivar, asexual reproduction of the new cultivar 'WILD THING' was first performed at a commercial nursery in Royal Oaks, Calif. in July of 2013. Softwood vegetative terminal cuttings were used for propagation. The inventor continued confidential, controlled evaluation and propagation of 'WILD THING', to establish a stable clone, with the most variegated foliage coloration. 'WILD THING' has since produced three generations and has shown that the unique features of this cultivar are stable and reproduced true to type. Typical asexual reproduction of the new variety is by softwood vegetative cuttings.

SUMMARY OF THE INVENTION

The cultivar 'WILD THING' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'WILD THING'. These characteristics in combination distinguish 'WILD THING' as a new and distinct *Leucadendron* cultivar:

1. yellow-green foliage with maroon center streaking.
2. Floral bracts are bright yellow green with strong orange-salmon flushing and dark greyed-purple central streaking.
3. Slower growth, relatively dense and compact habit.

PARENTAL COMPARISON

Plants of the new cultivar 'WILD THING' are similar to the parent in most horticultural characteristics. However, 'WILD THING' differs in producing foliage distinctively yellow-green with a maroon center streaking. Foliage of 'Ebony' is solid dark maroon. Floral Bracts of the new variety are a much brighter, vibrant color.

COMMERCIAL COMPARISON

Plants of the new cultivar 'WILD THING' can be compared to the well-known commercial variety *Leucadendron* 'Jester', unpatented. Plants of 'WILD THING' are similar to plants of 'Jester' in some horticultural characteristics, however, plants of 'WILD THING' differ in the following:

1. Plants of the new variety have darker foliage color, yellow-green with a maroon center, foliage of Jester is yellow with a green center.
2. Floral bract color of the new variety is deeper, more intense than floral bract color of 'Jester'.
3. The new variety is faster growing than 'Jester'.

Plants of the new cultivar 'WILD THING' can be compared to *Leucadendron* 'Safari Sunset', unpatented. The new variety is similar in some horticultural characteristics. However, the plants of 'WILD THING' differ in the following:

1. Foliage of 'Safari Sunset' is solid green, the new variety has variegated foliage.
2. Flowering bract color of the new variety is variegated yellow-green, greyed-purple with an orange flush. Flowering bract color of 'Safari Sunset' is solid red.
3. Plants of the new variety are more compact than plants of 'Safari Sunset'.

BRIEF DESCRIPTION OF THE PHOTOGRAPH

The accompanying photograph was taken using conventional techniques and although colors may appear different from actual colors due to light reflectance it is as accurate as possible by conventional photographic techniques. The accompanying photograph illustrates in full color foliage, floral bract and a forming cone of the new variety. Age of the plant photographed is approximately 2 years.

DETAILED BOTANICAL DESCRIPTION

In the following description, color references are made to The Royal Horticultural Society Colour Chart, 2007, except where general terms of ordinary dictionary significance are used. The following observations and measurements describe 'WILD THING' plants grown at a commercial nursery in Royal Oaks, Calif., under bright, unshaded conditions. Average day temperatures were approximately 8° C. to 26° C. and the average night temperature was approximately 3° C. to 18° C. No artificial light, photoperiodic treatments or chemical treatments were given to the plants. Measurements and numerical values represent averages of typical plant types.

Botanical classification: *Leucadendron salignum* x *laurolum* 'WILD THING'.

Age of the plant described: Approximately 2 years.

Container size of the plant described: 1 gallon commercial container.

PROPAGATION

Propagation method: Terminal cuttings, hardwood or semi-softwood.

Time to develop roots suitable for transplanting: About 6 to 8 weeks at an average temperature around 25° C.

Root description: Woody, not well branched, colored near Brown N199A and Grey-Brown 199A and 199B. Typically shallow rooted.

PLANT

Growth habit: Upright shrub.

Age of plant described: Approximately 15 months.

In a container or in the ground: 1 gallon container.

Height: 47 cm.

Plant spread: 36 cm.

Growth rate: Approximately 1 year to reach 30 cm in height.

Branching characteristics: An un-pinched plant has a central strong stem, with strong lateral branches occurring 4 or 5 at a single node. Lateral branch angle of attachment is highly variable, 15 to 90° from the central stem.

Central stem description:

- *Length*.—Approximately 36 cm.
- *Diameter*.—About 2.2 cm at base, about 0.9 cm uppermost section.
- *Color*.—Base (older wood) near Greyed-Orange 177D. Uppermost section near Greyed-Purple 187C.
- *Texture*.—Entire central stem glabrous, no scales, bark or lenticels observed.
- *Strength*.—Very strong and flexible.

Lateral branches:

- *Length of primary lateral branches*.—Approximately 15 cm on average.
- *Diameter of lateral branches*.—Approximately 0.5 to 0.8 cm.
- *Approximate quantity of lateral branches*.—12 to 15.
- *Branching arrangement*.—Whorled.
- *Texture*.—Glabrous.
- *Color*.—Lower section near Greyed-Purple 187C, upper section near Greyed-Purple N187C flushed 186B.

FOLIAGE

Leaf:

- *Arrangement*.—Spiral.
- *Quantity*.—Approximately 25 to 50, per main branch, including sub-branches.
- *Average length*.—6.0 to 7.5 cm.
- *Average width*.—Approximately 2.0 cm.
- *Shape of blade*.—Oblanceolate.
- *Apex*.—Broadly acute or rounded.
- *Base*.—Truncate.
- *Margin*.—Entire.
- *Texture of top surface*.—Glabrous.
- *Texture of bottom surface*.—Glabrous.
- *Pubescence*.—None.
- *Aspect*.—Slight undulation or twist. Lower occurring leaves are more twisted.
- *Color*.—Young foliage upper side: Near RHS Green 137C, thick streak or steaks in center near Greyed-Purple N186A. Streaks occurs over approximately 50 to 75% of leaf blade. Very thin margin near Greyed-Purple 187C. Young foliage under side: Near RHS Green 137C, thick streak or steaks in center near Greyed-Purple N187A. Streaks occurs over approximately 50% of leaf blade. Very thin margin near Greyed-Purple 187C. Mature foliage upper side: Near RHS Green 137C, thick streak or steaks in center near Greyed-Purple N186A. Streaks occurs over approximately 30 to 50% of leaf blade. Very thin margin near Greyed-Purple 187C. Mature foliage under side: Near RHS Green 137C, thick streak or steaks in center near Greyed-Purple N187A. Streaks occurs over approximately 50% of leaf blade. Very thin margin near Greyed-Purple 187C.
- *Venation*.—Type: Pinnate. Venation color upper side: Indistinguishable from foliage coloration. Venation color under side: Indistinguishable from foliage coloration.
- *Petiole*.—No present, sessile.

FLOWER

Natural flowering season: Year round in temperate California conditions.

Begins flowering after how many years/months: About 1 year.

Inflorescence type and habit: Female only flowers. Minute flowers occurring in gently spiraling rows on conical spikes. Flowers tubular structure of fused petals, outwardly facing. Flower self-cleaning, persisting approximately 6 weeks on the spike.

Quantity of flowers per inflorescence: 45, occurring in 9 rows.

Inflorescence size:

- *Diameter*.—Approximately 1.7 cm.
- *Height*.—Approximately 2.0 cm.

Individual flowers:

Size:

- *Diameter*.—Approximately 1.5 mm.
- *Length*.—Approximately 1 mm.
- *Shape*.—

Petals:
*Petal arrangement*.—Rotate.
*Size*.—Length: 1 mm. Width: 1 mm.
*Margin*.—Entire.
*Apex*.—Rounded.
*Base*.—Fused.
*Petal quantity*.—Indistinguishable, single, minute structure.
*Texture*.—Glabrous.

Color:
*Petals*.—When opening: Inner surface: Near RHS Greyed-Purple N186A. Outer surface: Near RHS Greyed-Purple N186A. Fully opened: Inner surface: Near RHS Greyed-Purple N18&A. Outer surface: Near RHS Greyed-Purple N187A.

Bud:
*Shape*.—Ovate.
*Length*.—Approximately 0.5 mm.
*Diameter*.—Approximately 0.4 mm.
*Color*.—Near RHS Greyed-Purple N186A.

Basal bracts:
*Arrangement*.—Overlapping whorls, very tightly held.
*Shape*.—Half-circle.
*Length*.—Approximately 0.4 mm.
*Width*.—Approximately 0.7 mm.
*Color*.—Near RHS Greyed-Purple N186A.
*Appearance*.—Shiny, likely from pubescence.
*Texture*.—Very minutely pubescent.

Fragrance: None.

Involucral bracts:
*Number*.—Average range 10 to 12.
*Length*.—Approximately 0.6 cm.
*Width*.—Approximately 0.5 cm.
*Shape*.—Broad deltate to quadrate.
*Texture*.—Glabrous.
*Apex shape*.—Truncate or occasionally acute.
*Margin*.—Entire.
*Color*.—Near RHS Brown 200B.

Floral bracts:
*Description*.—Leaf like, occurring just below inflorescence.
*Quantity*.—Average range 5 to 6.
*Arrangement*.—Spiral.
*Average length*.—6.0 to 7.5 cm.
*Average width*.—Approximately 2.0 cm.
*Shape of blade*.—Oblanceolate.
*Apex*.—Broadly acute or rounded.
*Base*.—Truncate.
*Margin*.—Entire.
*Texture of top surface*.—Glabrous.
*Texture of bottom surface*.—Glabrous.
*Pubescence*.—None.
*Aspect*.—Slight undulation or twist. Lower occurring leaves are more twisted.
*Color*.—Upper surface: Base color near RHS Yellow-Green 146D, heavily flushed Red 42C, thin margin near Red 53A, thicker part of margin flushed Red 52C. Thick center streaks near Greyed-Purple N186A and 187A. Under surface: Base color near RHS Yellow-Green 146D, heavily flushed Orange 26B, thin margin near Red 53A, thicker part of margin flushed Red 52C. Thick center streaks near Greyed-Purple N186A and 187A.

Peduncle: Beginning from the lowermost floral bract.
*Length*.—Approximately 3 cm.
*Diameter*.—Approximately 0.5 cm.
*Texture*.—Glabrous.
*Color*.—Lower section near Greyed-Purple 187C.

REPRODUCTIVE ORGANS

Minute flowers with compressed productive organs. Reproductive organs not visible under a dissecting microscope.

OTHER CHARACTERISTICS

Seeds and fruits: No seeds/fruits observed.

Disease/pest resistance: Neither resistance nor susceptibility to the normal pests and diseases of *Leucadendron* has been observed.

Temperature tolerance: Tolerates low temperatures to approximately −9° C. Good high temperature tolerance, observed to at least 40° C.

What is claimed is:

1. A new and distinct cultivar of *Leucadendron salignum* x *laureolum* plant named 'WILD THING' as herein illustrated and described.

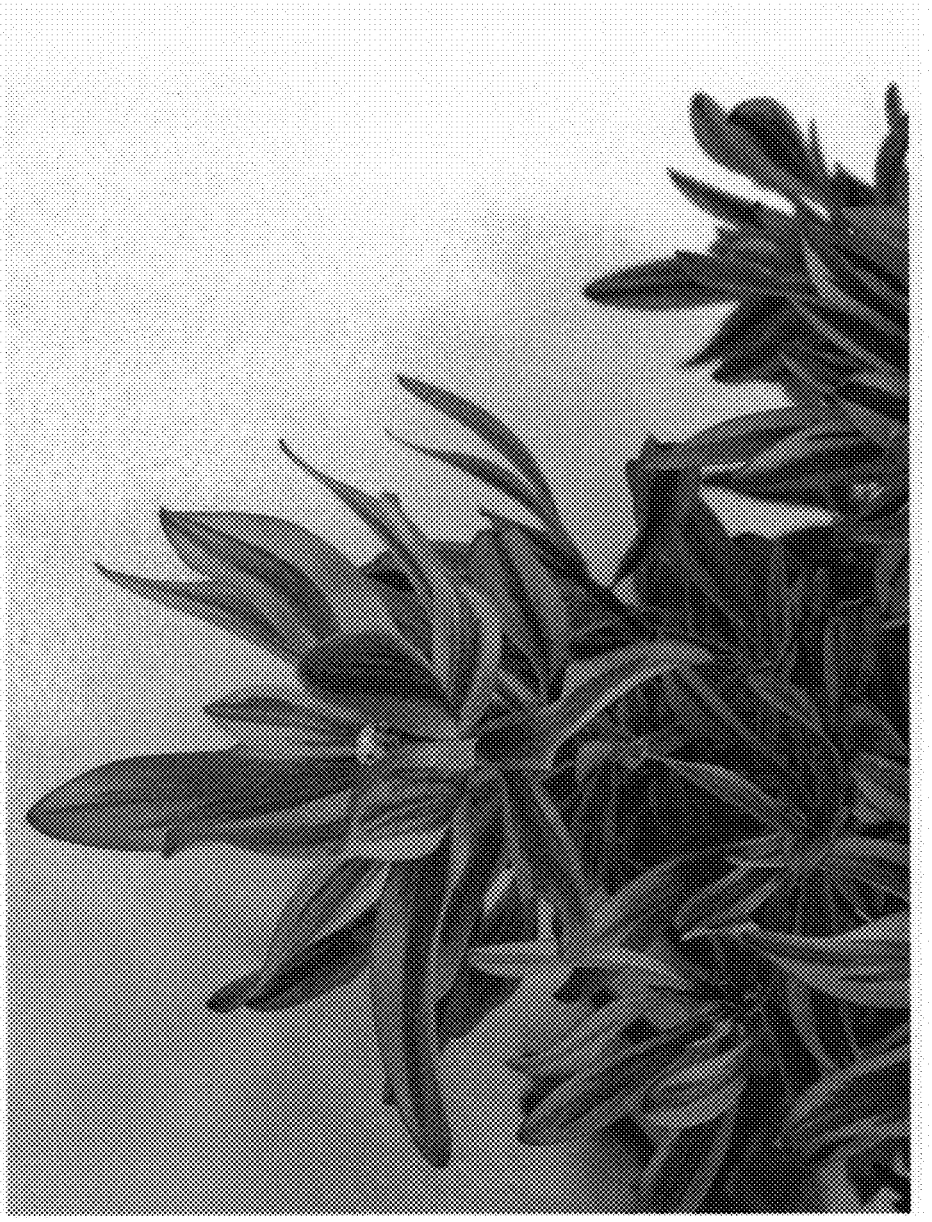

* * * * *